(12) United States Patent
Vogt et al.

(10) Patent No.: US 11,804,767 B2
(45) Date of Patent: Oct. 31, 2023

(54) MAGNETIC COUPLING ELEMENT WITH A MAGNETIC BEARING FUNCTION

(71) Applicant: KARDION GMBH, Stuttgart (DE)

(72) Inventors: Andreas Vogt, Renningen (DE); Armin Schuelke, Aidlingen (DE); Xiang Li, Ditzingen (DE); David Minzenmay, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 0 days.

(21) Appl. No.: 17/805,542

(22) Filed: Jun. 6, 2022

(65) Prior Publication Data

US 2022/0407403 A1  Dec. 22, 2022

Related U.S. Application Data

(63) Continuation of application No. 16/963,783, filed as application No. PCT/EP2019/051355 on Jan. 21, 2019, now Pat. No. 11,368,081.

(30) Foreign Application Priority Data

Jan. 24, 2018  (DE) .................... 10 2018 201 030.7

(51) Int. Cl.
*H02K 49/10* (2006.01)
*F16C 32/04* (2006.01)
*H02K 7/09* (2006.01)

(52) U.S. Cl.
CPC ......... *H02K 49/108* (2013.01); *F16C 32/047* (2013.01); *H02K 7/09* (2013.01)

(58) Field of Classification Search
CPC ...... H02K 49/108; H02K 7/09; F16C 32/047; F16C 32/0425; A61M 60/419; H01F 7/0242; F04D 13/024
(Continued)

(56) References Cited

U.S. PATENT DOCUMENTS 2,254,698 A  9/1941  Hansen, Jr.
3,085,407 A  4/1963  Tomlinson
(Continued)

FOREIGN PATENT DOCUMENTS

AU  7993698  2/1999
AU  2002308409  12/2005
(Continued)

OTHER PUBLICATIONS

JP 2013013216 (Year: 2013).*
(Continued)

*Primary Examiner* — Ahmed Elnakib
(74) *Attorney, Agent, or Firm* — Knobbe Martens Olson & Bear LLP

(57) ABSTRACT

The invention relates to a magnetic coupling element (100) with a magnetic bearing function. The magnetic coupling element (100) has a drive-side coupling magnet (109) arranged on a drive shaft (106), and also an output-side coupling magnet (115) arranged on an output shaft (112), the output-side coupling magnet (115) being magnetically coupled to the drive-side coupling magnet (109), and finally a bearing magnet ring (118) which is non-rotatably mounted with respect to the drive-side or output-side coupling magnet (109) or (115), a bearing magnet portion (133, 136) of the bearing magnet ring (118) having the same polarity as a coupling magnet portion (127, 130) opposite the bearing magnet portion (136).

20 Claims, 3 Drawing Sheets

(58) Field of Classification Search
USPC ...................................................... 310/90.5
See application file for complete search history.

(56) References Cited

U.S. PATENT DOCUMENTS

| | | |
|---|---|---|
| 3,505,987 A | 4/1970 | Heilman |
| 3,568,659 A | 3/1971 | Karnegis |
| 3,614,181 A | 10/1971 | Meeks |
| 3,645,268 A | 2/1972 | Capote |
| 3,747,998 A | 7/1973 | Klein et al. |
| 3,807,813 A * | 4/1974 | Milligan ............ H01F 1/04 |
| | | 310/90.5 |
| 3,995,617 A | 12/1976 | Watkins et al. |
| 4,115,040 A | 9/1978 | Knorr |
| 4,441,210 A | 4/1984 | Hochmair et al. |
| 4,471,252 A | 9/1984 | West |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A | 7/1989 | Wampler et al. |
| 4,888,009 A | 12/1989 | Lederman et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,985,014 A | 1/1991 | Orejola |
| 5,000,177 A | 3/1991 | Hoffmann et al. |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,289,821 A | 3/1994 | Swartz |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,629,661 A | 5/1997 | Ooi et al. |
| 5,690,674 A | 11/1997 | Diaz |
| 5,695,471 A | 12/1997 | Wampler |
| 5,713,954 A | 2/1998 | Rosenberg et al. |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,843,141 A | 12/1998 | Bischoff et al. |
| 5,888,241 A | 3/1999 | Jarvik |
| 5,888,242 A | 3/1999 | Antaki et al. |
| 5,904,646 A | 5/1999 | Jarvik |
| 5,911,685 A | 6/1999 | Siess et al. |
| 5,921,913 A | 7/1999 | Siess |
| 5,964,694 A | 10/1999 | Siess et al. |
| 6,001,056 A | 12/1999 | Jassawalla et al. |
| 6,007,478 A | 12/1999 | Siess et al. |
| 6,018,208 A | 1/2000 | Maher et al. |
| 6,050,975 A | 4/2000 | Poirier |
| 6,058,958 A | 5/2000 | Benkowski et al. |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A * | 11/2000 | Abe ............ F04C 23/008 |
| | | 418/94 |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,212,430 B1 | 4/2001 | Kung et al. |
| 6,217,541 B1 | 4/2001 | Yu |
| 6,220,832 B1 | 4/2001 | Schob |
| 6,224,540 B1 | 5/2001 | Lederman et al. |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,324,430 B1 | 11/2001 | Zarinetchi et al. |
| 6,324,431 B1 | 11/2001 | Zarinetchi et al. |
| 6,351,048 B1 | 2/2002 | Schob et al. |
| 6,361,292 B1 | 3/2002 | Chang et al. |
| 6,366,817 B1 | 4/2002 | Kung |
| 6,389,318 B1 | 5/2002 | Zarinetchi et al. |
| 6,398,734 B1 | 6/2002 | Cimochowski et al. |
| 6,400,991 B1 | 6/2002 | Kung |
| 6,432,136 B1 | 8/2002 | Weiss et al. |
| 6,442,434 B1 | 8/2002 | Zarinetchi et al. |
| 6,445,956 B1 | 9/2002 | Laird et al. |
| 6,447,266 B2 | 9/2002 | Antaki et al. |
| 6,471,713 B1 | 10/2002 | Vargas et al. |
| 6,496,733 B2 | 12/2002 | Zarinetchi et al. |
| 6,508,756 B1 | 1/2003 | Kung et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,561,975 B1 | 5/2003 | Pool et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,623,475 B1 | 9/2003 | Siess |
| 6,719,791 B1 | 4/2004 | Nüsser et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 6,979,338 B1 | 12/2005 | Loshakove et al. |
| 7,014,620 B2 | 3/2006 | Kim |
| 7,027,875 B2 | 4/2006 | Siess et al. |
| 7,011,620 B1 | 5/2006 | Siess |
| 7,062,331 B2 | 6/2006 | Zarinetchi et al. |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,155,291 B2 | 12/2006 | Zarinetchi et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,338,521 B2 | 3/2008 | Antaki et al. |
| 7,462,019 B1 | 12/2008 | Allarie et al. |
| 7,479,102 B2 | 1/2009 | Jarvik |
| 7,502,648 B2 | 3/2009 | Okubo et al. |
| 7,513,864 B2 | 4/2009 | Kantrowitz et al. |

(56) References Cited

U.S. PATENT DOCUMENTS

| | | |
|---|---|---|
| 7,520,850 B2 | 4/2009 | Brockway |
| 7,736,296 B2 | 6/2010 | Siess et al. |
| 7,762,941 B2 | 7/2010 | Jarvik |
| 7,794,384 B2 | 9/2010 | Sugiura et al. |
| 7,798,952 B2 | 9/2010 | Tansley et al. |
| 7,819,916 B2 | 10/2010 | Yaegashi |
| 7,841,976 B2 | 11/2010 | McBride et al. |
| 7,850,593 B2 | 12/2010 | Vincent et al. |
| 7,878,967 B1 | 2/2011 | Khanal |
| 7,934,909 B2 | 2/2011 | Jenson |
| 7,914,436 B1 | 3/2011 | Kung |
| 7,942,805 B2 | 5/2011 | Shambaugh, Jr. |
| 7,959,551 B2 | 6/2011 | Jarvik |
| 7,963,905 B2 | 6/2011 | Salmonsen et al. |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,231,519 B2 | 7/2012 | Reichenbach et al. |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,489,200 B2 | 7/2013 | Zarinetchi et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,608,635 B2 | 12/2013 | Yomtov et al. |
| 8,612,002 B2 | 12/2013 | Faltys et al. |
| 8,617,239 B2 | 12/2013 | Reitan |
| 8,620,447 B2 | 12/2013 | D'Ambrosio et al. |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,766,788 B2 | 7/2014 | D'Ambrosio |
| 8,814,933 B2 | 8/2014 | Siess |
| 8,827,890 B2 | 9/2014 | Lee et al. |
| 8,862,232 B2 | 10/2014 | Zarinetchi et al. |
| 8,864,642 B2 | 10/2014 | Scheckel |
| 8,864,643 B2 | 10/2014 | Reichenbach et al. |
| 8,864,644 B2 | 10/2014 | Yomtov |
| 8,870,739 B2 | 10/2014 | LaRose et al. |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,114 B2 | 12/2014 | Tansley et al. |
| 8,900,115 B2 | 12/2014 | Bolling et al. |
| 8,932,246 B2 | 1/2015 | Ferrari |
| 8,961,389 B2 | 2/2015 | Zilbershlag |
| 8,992,406 B2 | 3/2015 | Corbett |
| 8,992,407 B2 | 3/2015 | Smith et al. |
| 9,002,468 B2 | 4/2015 | Shea et al. |
| 9,002,469 B2 | 4/2015 | D'Ambrosio |
| 9,028,216 B2 | 5/2015 | Schumacher et al. |
| 9,028,392 B2 | 5/2015 | Shifflette |
| 9,033,863 B2 | 5/2015 | Jarvik |
| 9,071,182 B2 | 6/2015 | Yoshida et al. |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,220,826 B2 | 12/2015 | D'Ambrosio |
| 9,265,870 B2 | 2/2016 | Reichenbach et al. |
| 9,283,314 B2 | 3/2016 | Prasad et al. |
| 9,297,735 B2 | 3/2016 | Graichen et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,456,898 B2 | 10/2016 | Barnes et al. |
| 9,486,566 B2 | 11/2016 | Siess |
| 9,492,600 B2 | 11/2016 | Strueber et al. |
| 9,492,601 B2 | 11/2016 | Casas et al. |
| 9,533,084 B2 | 1/2017 | Siess et al. |
| 9,539,094 B2 | 1/2017 | Dale et al. |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,362 B2 | 2/2017 | Malinowski |
| 9,569,985 B2 | 2/2017 | Alkhatib et al. |
| 9,579,433 B2 | 2/2017 | LaRose et al. |
| 9,585,991 B2 | 3/2017 | Spence |
| 9,592,397 B2 | 3/2017 | Hansen et al. |
| 9,603,984 B2 | 3/2017 | Romero et al. |
| 9,616,107 B2 | 4/2017 | VanAntwerp et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,713,701 B2 | 7/2017 | Sarkar et al. |
| 9,717,831 B2 | 8/2017 | Schuermann |
| 9,724,083 B2 | 8/2017 | Quadri et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,800,172 B1 | 10/2017 | Leabman |
| 9,801,990 B2 | 10/2017 | Lynch |
| 9,814,813 B2 | 11/2017 | Corbett |
| 9,821,100 B2 | 11/2017 | Corbett et al. |
| 9,833,314 B2 | 12/2017 | Corbett |
| 9,833,550 B2 | 12/2017 | Siess |
| 9,833,611 B2 | 12/2017 | Govea et al. |
| 9,848,899 B2 | 12/2017 | Sliwa et al. |
| 9,849,223 B2 | 12/2017 | LaRose |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,143,571 B2 | 12/2018 | Spence et al. |
| 10,179,197 B2 | 1/2019 | Kaiser et al. |

(56) References Cited

U.S. PATENT DOCUMENTS

| | | | |
|---|---|---|---|
| 10,201,645 | B2 | 2/2019 | Muller |
| 10,207,038 | B2 | 2/2019 | Neumann |
| 10,220,129 | B2 | 3/2019 | Ayre et al. |
| 10,232,099 | B2 | 3/2019 | Peters et al. |
| 10,238,782 | B2 | 3/2019 | Barry |
| 10,238,783 | B2 | 3/2019 | Aboul-Hosn et al. |
| 10,251,986 | B2 | 4/2019 | Larose et al. |
| 10,279,093 | B2 | 5/2019 | Reichenbach et al. |
| 10,293,090 | B2 | 5/2019 | Bonde et al. |
| 10,300,185 | B2 | 5/2019 | Aboul-Hosn et al. |
| 10,300,249 | B2 | 5/2019 | Tao et al. |
| 10,322,217 | B2 | 6/2019 | Spence |
| 10,342,906 | B2 | 7/2019 | D'Ambrosio et al. |
| 10,357,598 | B2 | 7/2019 | Aboul-Hosn et al. |
| 10,361,617 | B2 | 7/2019 | Mueller et al. |
| 10,371,150 | B2 | 8/2019 | Wu et al. |
| 10,376,162 | B2 | 8/2019 | Edelman et al. |
| 10,420,869 | B2 | 9/2019 | Cornen |
| 10,434,232 | B2 | 10/2019 | Wu et al. |
| 10,449,275 | B2 | 10/2019 | Corbett |
| 10,449,279 | B2 | 10/2019 | Muller |
| 10,463,508 | B2 | 11/2019 | Spence et al. |
| 10,478,538 | B2 | 11/2019 | Scheckel et al. |
| 10,478,539 | B2 | 11/2019 | Pfeffer et al. |
| 10,478,542 | B2 | 11/2019 | Jahangir |
| 10,512,537 | B2 | 12/2019 | Corbett et al. |
| 10,525,178 | B2 | 1/2020 | Zeng |
| 10,537,670 | B2 | 1/2020 | Tuseth et al. |
| 10,537,672 | B2 | 1/2020 | Tuseth et al. |
| 10,557,475 | B2 | 2/2020 | Roehn |
| 10,561,771 | B2 | 2/2020 | Heilman et al. |
| 10,561,772 | B2 | 2/2020 | Schumacher |
| 10,576,191 | B2 | 3/2020 | LaRose |
| 10,584,589 | B2 | 3/2020 | Schumacher et al. |
| 10,589,012 | B2 | 3/2020 | Toellner et al. |
| 10,589,013 | B2 | 3/2020 | Bourque |
| 10,610,626 | B2 | 4/2020 | Spanier et al. |
| 10,617,808 | B2 | 4/2020 | Hastie et al. |
| 10,632,241 | B2 | 4/2020 | Schenck et al. |
| 10,660,998 | B2 | 5/2020 | Hodges |
| 10,662,967 | B2 | 5/2020 | Scheckel |
| 10,668,195 | B2 | 6/2020 | Flores |
| 10,669,855 | B2 | 6/2020 | Toellner et al. |
| 10,857,273 | B2 | 12/2020 | Hodges et al. |
| 11,000,282 | B2 | 5/2021 | Schuelke et al. |
| 11,033,729 | B2 | 6/2021 | Scheckel et al. |
| 11,045,638 | B2 | 6/2021 | Keenan et al. |
| 11,056,878 | B2 | 7/2021 | Gao et al. |
| 11,058,863 | B2 | 7/2021 | Demou |
| 11,058,865 | B2 | 7/2021 | Fitzgerald et al. |
| 11,065,434 | B2 | 7/2021 | Egler et al. |
| 11,065,437 | B2 | 7/2021 | Aber et al. |
| 11,092,158 | B2 | 8/2021 | Siess et al. |
| 11,097,092 | B2 | 8/2021 | Siess et al. |
| 11,103,689 | B2 | 8/2021 | Siess et al. |
| 11,103,690 | B2 | 8/2021 | Epple |
| 11,103,715 | B2 | 8/2021 | Fort |
| 11,107,626 | B2 | 8/2021 | Siess et al. |
| 11,110,265 | B2 | 9/2021 | Johnson |
| 11,123,538 | B2 | 9/2021 | Epple et al. |
| 11,123,539 | B2 | 9/2021 | Pfeffer et al. |
| 11,123,541 | B2 | 9/2021 | Corbett et al. |
| 11,129,978 | B2 | 9/2021 | Pfeffer et al. |
| 11,141,579 | B2 | 10/2021 | Steingräber |
| 11,160,970 | B2 | 11/2021 | Muller et al. |
| 11,167,124 | B2 | 11/2021 | Pfeffer et al. |
| 11,173,297 | B2 | 11/2021 | Muller |
| 11,179,557 | B2 | 11/2021 | Georges et al. |
| 11,179,559 | B2 | 11/2021 | Hansen |
| 11,185,678 | B2 | 11/2021 | Smith et al. |
| 11,185,680 | B2 | 11/2021 | Tuval et al. |
| 11,191,944 | B2 | 12/2021 | Tuval et al. |
| 11,197,989 | B2 | 12/2021 | Arslan et al. |
| 11,202,901 | B2 | 12/2021 | Barry |
| 11,219,756 | B2 | 1/2022 | Tanner et al. |
| 11,224,737 | B2 | 1/2022 | Petersen et al. |
| 11,229,786 | B2 | 1/2022 | Zeng et al. |
| 11,235,138 | B2 | 2/2022 | Gross-Hardt et al. |
| 11,235,140 | B2 | 2/2022 | Siess et al. |
| 11,241,568 | B2 | 2/2022 | Keenan et al. |
| 11,241,569 | B2 | 2/2022 | Delgado, III |
| 11,253,693 | B2 | 2/2022 | Pfeffer et al. |
| 11,260,212 | B2 | 3/2022 | Tuval et al. |
| 11,260,213 | B2 | 3/2022 | Zeng et al. |
| 11,273,300 | B2 | 3/2022 | Schafir |
| 11,273,301 | B2 | 3/2022 | Pfeffer et al. |
| 11,278,711 | B2 | 3/2022 | Liebing |
| 11,280,345 | B2 | 3/2022 | Bredenbreuker et al. |
| 11,285,309 | B2 | 3/2022 | Tuval et al. |
| 11,291,824 | B2 | 4/2022 | Schwammenthal et al. |
| 11,291,825 | B2 | 4/2022 | Tuval et al. |
| 11,291,826 | B2 | 4/2022 | Tuval et al. |
| 11,298,519 | B2 | 4/2022 | Josephy et al. |
| 11,298,520 | B2 | 4/2022 | Schwammenthal et al. |
| 11,298,521 | B2 | 4/2022 | Schwammenthal et al. |
| 11,298,523 | B2 | 4/2022 | Tuval et al. |
| 11,298,524 | B2 | 4/2022 | El Katerji et al. |
| 11,298,525 | B2 | 4/2022 | Jahangir |
| 11,305,103 | B2 | 4/2022 | Larose et al. |
| 11,305,105 | B2 | 4/2022 | Corbett et al. |
| 11,311,711 | B2 | 4/2022 | Casas et al. |
| 11,311,712 | B2 | 4/2022 | Zeng et al. |
| 11,313,228 | B2 | 4/2022 | Schumacher et al. |
| D951,435 | S | 5/2022 | Motomura et al. |
| 11,317,988 | B2 | 5/2022 | Hansen et al. |
| 11,318,295 | B2 | 5/2022 | Reyes et al. |
| 11,324,940 | B2 | 5/2022 | Earles et al. |
| 11,324,941 | B2 | 5/2022 | Xu et al. |
| 11,331,465 | B2 | 5/2022 | Epple |
| 11,331,466 | B2 | 5/2022 | Keen et al. |
| 11,331,467 | B2 | 5/2022 | King et al. |
| 11,331,470 | B2 | 5/2022 | Muller et al. |
| 11,338,124 | B2 | 5/2022 | Pfeffer et al. |
| 11,338,125 | B2 | 5/2022 | Liu et al. |
| 11,344,716 | B2 | 5/2022 | Taskin |
| 11,344,717 | B2 | 5/2022 | Kallenbach et al. |
| 11,351,359 | B2 | 6/2022 | Clifton et al. |
| 11,351,360 | B2 | 6/2022 | Rudser et al. |
| 11,357,967 | B2 | 6/2022 | Zeng et al. |
| 11,364,373 | B2 | 6/2022 | Corbett et al. |
| 11,368,081 | B2 | 6/2022 | Vogt et al. |
| 11,369,785 | B2 | 6/2022 | Callaway et al. |
| 11,369,786 | B2 | 6/2022 | Menon et al. |
| 11,389,639 | B2 | 7/2022 | Casas |
| 11,389,641 | B2 | 7/2022 | Nguyen et al. |
| 11,406,483 | B2 | 8/2022 | Wirbisky et al. |
| 11,406,520 | B2 | 8/2022 | Lam |
| 11,406,802 | B2 | 8/2022 | DeGraaf et al. |
| 11,413,443 | B2 | 8/2022 | Hodges et al. |
| 11,413,444 | B2 | 8/2022 | Nix et al. |
| 11,413,446 | B2 | 8/2022 | Siess et al. |
| 11,415,150 | B2 | 8/2022 | Richert et al. |
| 11,428,236 | B2 | 8/2022 | McBride et al. |
| 11,434,921 | B2 | 9/2022 | McBride et al. |
| 11,439,806 | B2 | 9/2022 | Kimball et al. |
| 11,446,481 | B2 | 9/2022 | Wolman et al. |
| 11,446,482 | B2 | 9/2022 | Kirchhoff et al. |
| 11,452,859 | B2 | 9/2022 | Earles et al. |
| 11,460,030 | B2 | 10/2022 | Shambaugh et al. |
| 11,471,662 | B2 | 10/2022 | Akkerman et al. |
| 11,471,663 | B2 | 10/2022 | Tuval et al. |
| 11,471,665 | B2 | 10/2022 | Clifton et al. |
| 11,471,692 | B2 | 10/2022 | Aghassian et al. |
| 11,478,627 | B2 | 10/2022 | Siess et al. |
| 11,478,628 | B2 | 10/2022 | Muller et al. |
| 11,478,629 | B2 | 10/2022 | Harjes et al. |
| 11,484,698 | B2 | 11/2022 | Radman |
| 11,484,699 | B2 | 11/2022 | Tuval et al. |
| 11,491,320 | B2 | 11/2022 | Siess |
| 11,491,322 | B2 | 11/2022 | Muller et al. |
| 11,497,896 | B2 | 11/2022 | Tanner et al. |
| 11,497,906 | B2 | 11/2022 | Grace et al. |
| 11,511,101 | B2 | 11/2022 | Hastie et al. |
| 11,511,103 | B2 | 11/2022 | Salahieh et al. |

(56) References Cited

U.S. PATENT DOCUMENTS

| | | |
|---|---|---|
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,740 B2 | 12/2022 | Agarwa et al. |
| 11,524,165 B2 | 12/2022 | Tan et al. |
| 11,529,062 B2 | 12/2022 | Moyer et al. |
| 11,529,508 B2 | 12/2022 | Jablonsk et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,596,727 B2 | 3/2023 | Siess et al. |
| 11,602,627 B2 | 3/2023 | Leonhardt |
| 11,628,293 B2 | 4/2023 | Gandhi et al. |
| 11,632,015 B2 | 4/2023 | Sconzert et al. |
| 11,638,813 B2 | 5/2023 | West |
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,699,551 B2 | 7/2023 | Diekhans et al. |
| 2001/0009645 A1 | 7/2001 | Noda |
| 2001/0041934 A1 | 11/2001 | Yamazaki et al. |
| 2002/0147495 A1 | 10/2002 | Petroff |
| 2002/0153664 A1 | 10/2002 | Schroeder |
| 2002/0177324 A1 | 11/2002 | Metzler |
| 2003/0040765 A1 | 2/2003 | Breznock |
| 2003/0091450 A1 | 5/2003 | Davis et al. |
| 2003/0111800 A1 | 6/2003 | Kreutzer |
| 2003/0125766 A1 | 7/2003 | Ding |
| 2003/0130581 A1 | 7/2003 | Salo et al. |
| 2003/0139643 A1 | 7/2003 | Smith et al. |
| 2003/0191357 A1 | 10/2003 | Frazier |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0167410 A1 | 8/2004 | Hettrick |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0019167 A1 | 1/2005 | Nusser et al. |
| 2005/0085683 A1 | 4/2005 | Bolling et al. |
| 2005/0107847 A1 | 5/2005 | Gruber et al. |
| 2005/0220636 A1 | 10/2005 | Henein et al. |
| 2006/0004423 A1 | 1/2006 | Boveja et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0190036 A1 | 8/2006 | Wendel et al. |
| 2006/0196277 A1 | 9/2006 | Allen et al. |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0129767 A1 | 6/2007 | Wahlstrand |
| 2007/0142696 A1 | 6/2007 | Crosby et al. |
| 2007/0156006 A1 | 7/2007 | Smith et al. |
| 2007/0282209 A1 | 12/2007 | Lui et al. |
| 2008/0015481 A1 | 1/2008 | Bergin et al. |
| 2008/0015517 A1 | 1/2008 | Geistert et al. |
| 2008/0058925 A1 | 3/2008 | Cohen |
| 2008/0079392 A1 | 4/2008 | Baarman et al. |
| 2008/0082005 A1 | 4/2008 | Stern et al. |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0266922 A1 | 10/2008 | Mumtaz et al. |
| 2008/0292478 A1 | 11/2008 | Baykut et al. |
| 2009/0004037 A1 | 1/2009 | Ito |
| 2009/0010462 A1 | 1/2009 | Ekchian et al. |
| 2009/0024042 A1 | 1/2009 | Nunez et al. |
| 2009/0112312 A1 | 4/2009 | Larose et al. |
| 2009/0138080 A1 | 5/2009 | Siess et al. |
| 2009/0198307 A1 | 8/2009 | Mi et al. |
| 2009/0198312 A1 | 8/2009 | Barker |
| 2009/0203957 A1 | 8/2009 | LaRose et al. |
| 2009/0204205 A1 | 8/2009 | Larose et al. |
| 2009/0276016 A1 | 11/2009 | Phillips et al. |
| 2009/0312650 A1 | 12/2009 | Maile et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0331918 A1 | 12/2010 | Digiore et al. |
| 2011/0137394 A1 | 6/2011 | Lunsford et al. |
| 2011/0184224 A1 | 7/2011 | Garrigue |
| 2011/0224720 A1 | 9/2011 | Kassab et al. |
| 2011/0230821 A1 | 9/2011 | Babic |
| 2011/0237863 A1 | 9/2011 | Ricci et al. |
| 2011/0238172 A1 | 9/2011 | Akdis |
| 2012/0022645 A1 | 1/2012 | Burke |
| 2012/0050931 A1 | 3/2012 | Terry et al. |
| 2012/0088954 A1 | 4/2012 | Foster |
| 2012/0093628 A1 | 4/2012 | Liebing |
| 2012/0134793 A1 | 5/2012 | Wu et al. |
| 2012/0158074 A1 | 6/2012 | Hall |
| 2012/0172655 A1 | 7/2012 | Campbell et al. |
| 2012/0178986 A1 | 7/2012 | Campbell et al. |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0085318 A1 | 4/2013 | Toellner |
| 2013/0099585 A1 | 4/2013 | Von Novak et al. |
| 2013/0116575 A1 | 5/2013 | Mickle et al. |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303832 A1 | 11/2013 | Wampler |
| 2013/0303970 A1 | 11/2013 | Keenan et al. |
| 2013/0330219 A1 | 12/2013 | LaRose et al. |
| 2014/0005467 A1 | 1/2014 | Farnan et al. |
| 2014/0012282 A1 | 1/2014 | Fritsch |
| 2014/0039587 A1 | 2/2014 | Romero |
| 2014/0051908 A1 | 2/2014 | Khanal et al. |
| 2014/0063666 A1 | 3/2014 | Kallal et al. |
| 2014/0079557 A1 | 3/2014 | LaRose et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0233184 A1 | 8/2014 | Thompson et al. |
| 2014/0265620 A1 | 9/2014 | Hoarau et al. |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0028805 A1 | 1/2015 | Dearden et al. |
| 2015/0031936 A1 | 1/2015 | LaRose et al. |

(56) References Cited

U.S. PATENT DOCUMENTS

| | | |
|---|---|---|
| 2015/0051438 A1 | 2/2015 | Taskin |
| 2015/0090372 A1 | 4/2015 | Branagan et al. |
| 2015/0099923 A1 | 4/2015 | Magovern et al. |
| 2015/0190092 A1 | 7/2015 | Mori |
| 2015/0196076 A1 | 7/2015 | Billingslea |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0333532 A1 | 11/2015 | Han et al. |
| 2015/0343179 A1 | 12/2015 | Schumacher et al. |
| 2015/0380972 A1 | 12/2015 | Fort |
| 2016/0008531 A1 | 1/2016 | Wang et al. |
| 2016/0022889 A1 | 1/2016 | Bluvshtein et al. |
| 2016/0038663 A1 | 2/2016 | Taskin et al. |
| 2016/0045654 A1 | 2/2016 | Connor |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0144089 A1 | 5/2016 | Woo et al. |
| 2016/0144166 A1 | 5/2016 | Decré et al. |
| 2016/0166747 A1 | 6/2016 | Frazier et al. |
| 2016/0175501 A1 | 6/2016 | Schuermann |
| 2016/0213828 A1 | 7/2016 | Sievers |
| 2016/0223086 A1 | 8/2016 | Balsells et al. |
| 2016/0268846 A1 | 9/2016 | Akuzawa et al. |
| 2016/0271309 A1 | 9/2016 | Throckmorton et al. |
| 2016/0279311 A1 | 9/2016 | Cecere et al. |
| 2016/0331980 A1 | 11/2016 | Strommer et al. |
| 2016/0344302 A1 | 11/2016 | Inoue |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0047781 A1 | 2/2017 | Stanislawski et al. |
| 2017/0049947 A1 | 2/2017 | Corbett et al. |
| 2017/0070082 A1 | 3/2017 | Zheng et al. |
| 2017/0080136 A1 | 3/2017 | Janeczek et al. |
| 2017/0087286 A1 | 3/2017 | Spanier et al. |
| 2017/0087288 A1 | 3/2017 | Grob-Hardttim et al. |
| 2017/0128644 A1 | 5/2017 | Foster |
| 2017/0136164 A1 | 5/2017 | Yeatts |
| 2017/0136225 A1 | 5/2017 | Siess et al. |
| 2017/0143952 A1 | 5/2017 | Siess et al. |
| 2017/0143977 A1 | 5/2017 | Kaib et al. |
| 2017/0157309 A1 | 6/2017 | Begg et al. |
| 2017/0203104 A1 | 7/2017 | Nageri et al. |
| 2017/0209633 A1 | 7/2017 | Cohen |
| 2017/0231717 A1 | 8/2017 | Forsell |
| 2017/0271919 A1 | 9/2017 | Von Novak, III et al. |
| 2017/0274128 A1 | 9/2017 | Tamburino et al. |
| 2017/0275799 A1 | 9/2017 | Chen |
| 2017/0288448 A1 | 10/2017 | Kranz et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0354812 A1 | 12/2017 | Callaghan et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0078329 A1 | 3/2018 | Hansen et al. |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0250456 A1 | 9/2018 | Nitzan et al. |
| 2018/0256796 A1 | 9/2018 | Hansen |
| 2018/0256800 A1 | 9/2018 | Conyers et al. |
| 2018/0280598 A1 | 10/2018 | Curran et al. |
| 2018/0280708 A1 | 10/2018 | Escalona et al. |
| 2018/0289877 A1 | 10/2018 | Schumacher et al. |
| 2018/0303990 A1 | 10/2018 | Siess et al. |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1* | 1/2019 | Zhang .............. G01N 33/57484 |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0068004 A1 | 2/2019 | Louis |
| 2019/0076167 A1 | 3/2019 | Fantuzzi et al. |
| 2019/0083690 A1 | 3/2019 | Siess et al. |
| 2019/0097447 A1 | 3/2019 | Partovi |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0175808 A1 | 6/2019 | Zilbershlag et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0222064 A1 | 7/2019 | Du et al. |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2019/0393735 A1 | 12/2019 | Lee et al. |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |

(56) References Cited

U.S. PATENT DOCUMENTS

| | | |
|---|---|---|
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0054806 A1 | 2/2020 | Sun |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0139032 A1 | 5/2020 | Bryson et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0227954 A1 | 7/2020 | Ding et al. |
| 2020/0345337 A1 | 11/2020 | Muller et al. |
| 2021/0052793 A1 | 2/2021 | Struthers et al. |
| 2021/0057804 A1 | 2/2021 | Wenning |
| 2021/0143688 A1 | 5/2021 | Agrawal et al. |
| 2021/0236803 A1 | 8/2021 | Stotz |
| 2021/0268264 A1 | 9/2021 | Stotz |
| 2021/0290929 A1 | 9/2021 | Stotz |
| 2021/0290930 A1 | 9/2021 | Kasel |
| 2021/0290931 A1 | 9/2021 | Baumbach |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322011 A1 | 10/2021 | Schuelke et al. |
| 2021/0322756 A1 | 10/2021 | Vollmer et al. |
| 2021/0320958 A1 | 10/2021 | Stotz et al. |
| 2021/0336484 A1 | 10/2021 | Araujo et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0339009 A1 | 11/2021 | Stotz et al. |
| 2021/0346678 A1 | 11/2021 | Baumbach et al. |
| 2021/0346680 A1 | 11/2021 | Vogt et al. |
| 2021/0351628 A1 | 11/2021 | Araujo et al. |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0379360 A1 | 12/2021 | Schellenberg |
| 2021/0384812 A1 | 12/2021 | Vollmer et al. |
| 2021/0386990 A1 | 12/2021 | Stotz et al. |
| 2021/0393944 A1 | 12/2021 | Wenning |
| 2021/0399582 A1 | 12/2021 | Araujo et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0139614 A1 | 5/2022 | Diekhans et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0320901 A1 | 10/2022 | Araujo et al. |
| 2023/0001178 A1 | 1/2023 | Corbett et al. |
| 2023/0191141 A1 | 6/2023 | Wenning et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 796 357 | 10/2011 |
| CA | 3 000 581 | 4/2017 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 201150675 | 11/2008 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 103942511 | 7/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 106776441 | 5/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 26 24 058 | 12/1977 |
| DE | 3 545 214 | 7/1986 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 103 02 550 | 8/2004 |
| DE | 101 55 011 | 11/2005 |
| DE | 601 19 592 | 9/2006 |
| DE | 20 2005 020 288 | 6/2007 |
| DE | 10 2008 060 357 | 6/2010 |
| DE | 10 2009 039 658 | 3/2011 |
| DE | 20 2009 018 416 | 8/2011 |

(56) References Cited

FOREIGN PATENT DOCUMENTS

| | | |
|---|---|---|
| DE | 10 2012 200 912 | 7/2013 |
| DE | 10 2012 022 456 | 5/2014 |
| DE | 10 2013 007 562 | 11/2014 |
| DE | 11 2012 005 944 | 12/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2016 106 683 | 10/2016 |
| DE | 20 2015 009 422 | 7/2017 |
| DE | 10 2012 207 042 | 9/2017 |
| DE | 10 2016 013 334 | 4/2018 |
| DE | 102017212 193 | 1/2019 |
| DE | 10 2018 206 758 | 11/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 930 086 | 7/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 2 752 209 | 7/2014 |
| EP | 2 782 210 | 9/2014 |
| EP | 3 326 567 | 10/2014 |
| EP | 1 898 971 | 3/2015 |
| EP | 2 859 911 | 4/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 2 966 753 | 1/2016 |
| EP | 1 996 252 | 5/2016 |
| EP | 2 475 415 | 6/2016 |
| EP | 2 906 265 | 7/2016 |
| EP | 2 454 799 | 9/2016 |
| EP | 3 069 739 | 9/2016 |
| EP | 3 127 562 | 2/2017 |
| EP | 2 585 129 | 3/2017 |
| EP | 3 143 682 | 3/2017 |
| EP | 2 709 689 | 4/2017 |
| EP | 3 220 505 | 9/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 3 205 359 | 8/2018 |
| EP | 3 205 360 | 8/2018 |
| EP | 3 456 367 | 3/2019 |
| EP | 3 542 835 | 9/2019 |
| EP | 3 542 836 | 9/2019 |
| EP | 3 711 785 | 9/2020 |
| EP | 3 711 786 | 9/2020 |
| EP | 3 711 787 | 9/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 423 126 | 2/2021 |
| EP | 3 487 549 | 2/2021 |
| EP | 3 113 806 | 3/2021 |
| EP | 3 198 677 | 3/2021 |
| EP | 3 248 647 | 3/2021 |
| EP | 3 436 106 | 3/2021 |
| EP | 2 344 218 | 4/2021 |
| EP | 3 436 104 | 4/2021 |
| EP | 3 436 105 | 4/2021 |
| EP | 3 749 383 | 4/2021 |
| EP | 3 116 407 | 5/2021 |
| EP | 3 131 615 | 6/2021 |
| EP | 3 338 825 | 6/2021 |
| EP | 3 432 944 | 6/2021 |
| EP | 2 608 731 | 7/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 884 968 | 9/2021 |
| EP | 3 884 969 | 9/2021 |
| EP | 3 027 241 | 10/2021 |
| EP | 3 077 018 | 10/2021 |
| EP | 3 485 936 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 539 613 | 2/2022 |
| EP | 2 858 718 | 3/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 755 237 | 4/2022 |
| EP | 3 765 110 | 4/2022 |
| EP | 3 782 667 | 4/2022 |
| EP | 3 984 589 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 219 339 | 6/2022 |
| EP | 3 737 310 | 7/2022 |
| EP | 3 899 994 | 8/2022 |
| EP | 3 485 819 | 9/2022 |
| EP | 3 487 550 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 808 408 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 597 231 | 1/2023 |
| EP | 3 656 292 | 1/2023 |
| EP | 3 768 345 | 1/2023 |
| EP | 3 856 275 | 1/2023 |
| EP | 3 003 420 | 2/2023 |
| EP | 3 539 585 | 2/2023 |
| EP | 3 046 594 | 3/2023 |
| EP | 3 256 186 | 3/2023 |

(56) References Cited

FOREIGN PATENT DOCUMENTS

| | | |
|---|---|---|
| EP | 3 538 173 | 3/2023 |
| EP | 3 938 005 | 4/2023 |
| EP | 3 946 511 | 4/2023 |
| EP | 3 544 649 | 6/2023 |
| EP | 3 634 528 | 6/2023 |
| FR | 1458525 | 3/1966 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2003-019197 | 1/2003 |
| JP | 2004-278375 | 10/2004 |
| JP | 2005-028137 | 2/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6267625 | 1/2018 |
| JP | 2018-046708 | 3/2018 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2008/106103 | 9/2008 |
| WO | WO 2009/010888 | 1/2009 |
| WO | WO 2009/023905 | 2/2009 |
| WO | WO 2009/029977 | 3/2009 |
| WO | WO 2009/046789 | 4/2009 |
| WO | WO 2009/046790 | 4/2009 |
| WO | WO 2009/073037 | 6/2009 |
| WO | WO 2010/042054 | 4/2010 |
| WO | WO 2010/119267 | 10/2010 |
| WO | WO 2011/003043 | 1/2011 |
| WO | WO 2011/007300 | 1/2011 |
| WO | WO 2011/081626 | 7/2011 |
| WO | WO 2011/160858 | 12/2011 |
| WO | WO 2012/047540 | 4/2012 |
| WO | WO 2012/112129 | 8/2012 |
| WO | WO 2012/147061 | 11/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/152732 | 10/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/021846 | 2/2017 |
| WO | WO 2017/053988 | 3/2017 |
| WO | WO 2017/060257 | 4/2017 |
| WO | WO 2017/066257 | 4/2017 |
| WO | WO 2017/089440 | 6/2017 |
| WO | WO 2017/112695 | 6/2017 |
| WO | WO 2017/112698 | 6/2017 |
| WO | WO 2017/118738 | 7/2017 |
| WO | WO 2017/147291 | 8/2017 |
| WO | WO 2017/159849 | 9/2017 |
| WO | WO 2017/162619 | 9/2017 |
| WO | WO 2017/165372 | 9/2017 |
| WO | WO 2017/205909 | 12/2017 |
| WO | WO 2017/218349 | 12/2017 |
| WO | WO 2018/033799 | 2/2018 |
| WO | WO 2018/088939 | 3/2018 |
| WO | WO 2018/100192 | 6/2018 |
| WO | WO 2018/109038 | 6/2018 |
| WO | WO 2018/139508 | 8/2018 |
| WO | WO 2018/197306 | 11/2018 |
| WO | WO 2019/025258 | 2/2019 |
| WO | WO 2019/025259 | 2/2019 |
| WO | WO 2019/025260 | 2/2019 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/078723 | 4/2019 |
| WO | WO 2019/101786 | 5/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2019/183247 | 9/2019 |
| WO | WO 2019/185511 | 10/2019 |
| WO | WO 2019/185512 | 10/2019 |
| WO | WO 2018/135477 | 11/2019 |
| WO | WO 2018/135478 | 11/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/219868 | 11/2019 |
| WO | WO 2019/219871 | 11/2019 |

(56) References Cited

FOREIGN PATENT DOCUMENTS

| | | |
|---|---|---|
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/229224 | 12/2019 |
| WO | WO 2019/234146 | 12/2019 |
| WO | WO 2019/234151 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2019/244031 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/089429 | 5/2020 |
| WO | WO 2020/132211 | 6/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |

OTHER PUBLICATIONS

"ABMD—Taking a Closer Look at Impella ECP as the Pivotal Trial Gets Underway", Guggenheim, Press Release, Mar. 29, 2022, pp. 4.
International Search Report and Written Opinion received in PCT Application No. PCT/EP2019/051355, dated Apr. 26, 2019 in 17 pages.
International Preliminary Report on Patentability and Written Opinion received in PCT Application No. PCT/EP2019/051355, dated Aug. 6, 2020 in 20 pages.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.

* cited by examiner

MAGNETIC COUPLING ELEMENT WITH A MAGNETIC BEARING FUNCTION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The invention relates to a magnetic coupling element with a magnetic bearing function and to a or to a method for producing a magnetic coupling element with a magnetic bearing function of the type specified in the independent claims. The present invention also relates to a computer program.

Description of the Related Art

Magnetic coupling elements can be used in which opposing pairs of magnets are used to transmit torque without contact. In addition, diversion elements can also be used to guide a magnetic flux and thus increase the transmittable torque and improve the efficiency of the coupling element.

SUMMARY OF THE INVENTION

In light of this, the approach presented here introduces a magnetic coupling element with a magnetic bearing function, a method for producing a magnetic coupling element with a magnetic bearing function, a device which uses this method, and finally a corresponding computer program according to the main claims. The measures listed in the dependent claims allow advantageous embodiments and improvements of the device specified in the independent claim.

A bearing function can also be achieved in the radial direction, for example, by means of an additional bearing magnet ring which is arranged inside a magnetic coupling element so as to be offset from the coupling magnets.

A magnetic coupling element is presented which has a magnetic bearing function, the magnetic coupling element comprising the following features:

- a drive-side coupling magnet arranged on a drive shaft;
- an output-side coupling magnet arranged on an output shaft, the output-side coupling magnet being magnetically coupled to the drive-side coupling magnet; and
- a bearing magnet ring which is non-rotatably mounted with respect to the drive-side or output-side coupling magnet, at least one bearing magnet portion of the bearing magnet ring having the same polarity as a coupling magnet portion opposite the bearing magnet portion.

A drive shaft can be a rod-shaped machine element that is used to transmit rotary motion and torque and to support rotating parts. Coupling magnets can be a type of coupling element of which the torque transmission function is based on the action of a magnetic field or a coupled. An output shaft can be a machine element in which the power introduced via the gear mechanism can be tapped at the shaft end of said mechanism in the form of machine power. A bearing magnet ring can be an at least partially ring-shaped magnet which allows bearing without material contact by magnetic forces. Overall, it should be noted that the approach presented here advantageously allows permanent magnets to be used as magnets.

According to one embodiment, the bearing magnet ring and the drive-side or output-side coupling magnet have magnetic poles which attract one another in the axial direction and oppose one another so as to repel one another in the radial direction. This can result in a considerable reduction in friction losses, and there can be improvements in terms of efficiency, heat generation and wear.

According to one embodiment, the drive-side and the output-side coupling magnet can each have at least coupling magnet portions having a different polarity, in particular with the two coupling magnet portions being arranged or oriented in the axial direction. This can result in an improved carry-along effect by optimizing or aligning the magnetic flux lines in the magnetic coupling element.

According to one embodiment, the bearing magnet ring can comprise at least two bearing magnet ring portions of a different polarity, in particular with the two bearing magnet ring portions being arranged beside one another in the axial direction. In this case, such a structure of axially adjacent and mirror-image bearing magnet ring portions can be produced more cost-effectively and simply and/or can have an improved bearing function.

According to one embodiment, the bearing magnet ring can surround at least one portion of the drive-side or output-side coupling magnet. In this case, a relatively high repelling force and thus a stable bearing function can be achieved between the bearing magnet ring and the opposite drive-side or output-side coupling magnet which is spaced apart therefrom.

According to one embodiment, the bearing magnet ring portion can have an angular offset with respect to the opposite coupling magnet portion of the drive-side or output-side coupling magnet. In this case, the angular offset can be used to compensate for the rotation of the two shafts with respect to one another when torque is applied, during the bearing.

According to one embodiment, the drive-side or output-side coupling magnet can radially surround the bearing magnet ring. The magnetic fields radially emanating from the drive-side or output-side coupling magnet can be combined and the magnetic force between the individual parts of the magnetic coupling element can be amplified.

According to one embodiment, the bearing magnet ring can be separated from the drive-side or output-side coupling magnet by a tubular portion of a housing element. In this case, there can be a separation of media, in particular if the magnetic coupling element is intended to be used in regions around which fluid flows.

According to one embodiment, the housing element can be made from a non-magnetic metal or material and/or can be formed so as to be non-rotating or non-rotatable. A housing element of this kind allows losses due to magnetic reversal of the housing element to be avoided.

Furthermore, a method for producing a magnetic coupling element with a magnetic bearing function is presented, the method comprising the following steps:

providing the drive-side coupling magnet arranged on a drive shaft, the output-side coupling magnet arranged on an output shaft, and the bearing magnet ring; and
assembling the drive-side coupling magnet arranged on the drive shaft, the output-side coupling magnet arranged on an output shaft, and the bearing magnet ring in such a way that the output-side coupling magnet is magnetically coupled to the drive-side coupling magnet and the bearing magnet ring is non-rotatably mounted with respect to the drive-side or output-side coupling magnet, at least one bearing magnet portion of the bearing magnet ring having the same polarity as a coupling magnet portion opposite the bearing magnet portion, in order to produce a magnetic coupling element with a magnetic bearing function.

Said method can be implemented, for example, in software or hardware or in a mixture of software and hardware, for example in a controller.

The approach presented here further provides a device which is designed to execute, trigger or implement the steps of a variant of a method presented here in corresponding apparatuses. The problem addressed by the invention can also be quickly and efficiently solved by this variant of the invention in the form of a device.

For this purpose, the device can have at least one computing unit for processing signals or data, at least one memory unit for storing signals or data, at least one interface to a sensor or an actuator for reading in sensors signals from the sensor or for outputting data or control signals to the actuator and/or at least one communication interface for reading in or outputting data which are embedded in a communication protocol. The computing unit can be a signal processor, a microcontroller or the like, and the memory unit can be a flash memory, an EEPROM or a magnetic memory unit. The communication interface can be designed to read in or output data wirelessly and/or in a wired manner, it being possible for a communication interface which can read in or output data in a wired manner to read in said data from a corresponding data transmission line or output same into a corresponding data transmission line electrically or optically.

A device in the present case can be understood to mean an electrical device which processes sensor signals and outputs control and/or data signals on the basis thereof. The device can have an interface which is designed as hardware and/or as software. In the case of a hardware design, the interfaces can be part of a so-called ASIC system, for example, which includes a wide range of functions of the device. It is also possible, however, for the interfaces to consist of their own, integrated circuits or to at least partly consist of discrete components. In the case of a software design, the interfaces can be software modules which are present on a microcontroller, for example, in addition to other software modules.

A computer program product or a computer program having program code that can be stored on a machine-readable carrier or memory medium, such as a semiconductor memory, hard-disk memory or an optical memory, is used to execute, implement and/or trigger the steps of the method according to one of the above-described embodiments, in particular if the program product or program is executed on a computer or a device.

BRIEF DESCRIPTION OF THE DRAWINGS

Embodiments of the approach presented here are illustrated in the drawings and explained in more detail in the following description. In the drawings.

DETAILED DESCRIPTION

Figure 1:
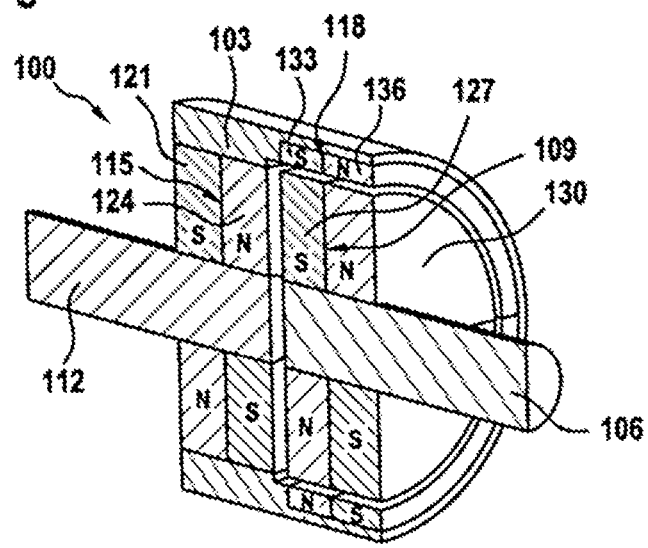
FIG. 1 is a schematic cross-sectional view of a magnetic coupling element with a magnetic bearing function according to one embodiment.

The magnetic coupling element 100 comprises a housing element 103, a drive-side coupling magnet 109 arranged on a drive shaft 106, an output-side coupling magnet 115 arranged on an output shaft 112, and a bearing magnet ring 118. The different poles of the coupling magnets 109 and 115 and the bearing magnet ring 118 are indicated with different colors, the north pole being indicated with an "N" and the south pole being indicated with an "S."

The output-side coupling magnet 115 is magnetically coupled to the drive-side coupling magnet 109. The drive-side and output-side coupling magnet 109 and 115 each have at least coupling magnet portions 121, 124, 127, 130 having a different polarization, the coupling magnet portions 121, 124, 127, 130 being arranged in particular in the axial direction. The bearing magnet ring 118 also comprises at least two bearing magnet ring portions 133, 136 having a different polarization, the two bearing magnet ring portions 133 and 136 also being arranged in particular in the axial direction. The bearing magnet ring 118 surrounds at least one portion 127 and 130 of the drive-side coupling magnet 109. The bearing magnet ring 118 is non-rotatably mounted with respect to the drive-side or output-side coupling magnet 109 and 115, each bearing magnet portion 133 and 136 of the bearing magnet ring 118 having the same polarization or polarity as a coupling magnet portion 127 and 130 opposite the bearing magnet portion 133 and 136. The bearing magnet ring 118 and the drive-side coupling magnet 109 have magnetic poles which attract one another in the axial direction and oppose one another so as to repel one another in the radial direction.

The drive shaft 106, which is a motor shaft according to one embodiment, and the output shaft 112 each carry magnetic dipoles, resulting in a preferably axially parallel magnetic flux. Since different poles attract one another, the output shaft 112 is carried along in the direction of rotation when the drive shaft 106 rotates. The axial force occurring in the process is absorbed by an axial bearing, which is not shown here. Magnetic yoke plates are also not shown in FIG. 1. Depending on the torque applied, the two shafts 106 and 112 rotate by several angular degrees with respect to one other.

In order to demonstrate a radial bearing function, the bearing magnet ring 118 is connected to one of the coupling magnets for conjoint rotation, this being the drive-side coupling magnet 109 according to one embodiment, in such a way that radially repelling poles oppose one another. The bearing magnet ring 118 is thus centered with respect to the drive-side coupling magnet 109. If this bearing is extended in an axially parallel manner, this arrangement can take over the complete radial bearing of a shaft. Care should be taken in this design that the coupling magnets 109 and 115 are designed to be considerably stronger than the bearing magnet ring 118 in order to ensure the transmission of torque. For instance, it can be ensured that the repelling or attracting forces of the coupling magnets 109 and 115 are not able to produce a rotation of the bearing magnet ring 118 on the shaft with respect to those in the housing element 103, which would lead to an attracting force between the bearing magnets. The coupling magnets 109 and 115 and the bearing magnet ring 118 can in principle also be magnetized in a 2-, 4-, 6- etc. poled manner.

The present magnetic coupling element 100 can be particularly advantageous in the case of all kinds of drives in which the transmission of torque is required without using a shaft to be sealed by a seal and for which, at the same time, radial bearing of the output-side coupling magnet 115 is required. This is the case, for example, in metering and micropumps for driving impeller-like rotors. A particular advantage is provided for driving in which drive-side and output-side media separation is desired.

Figure 2:
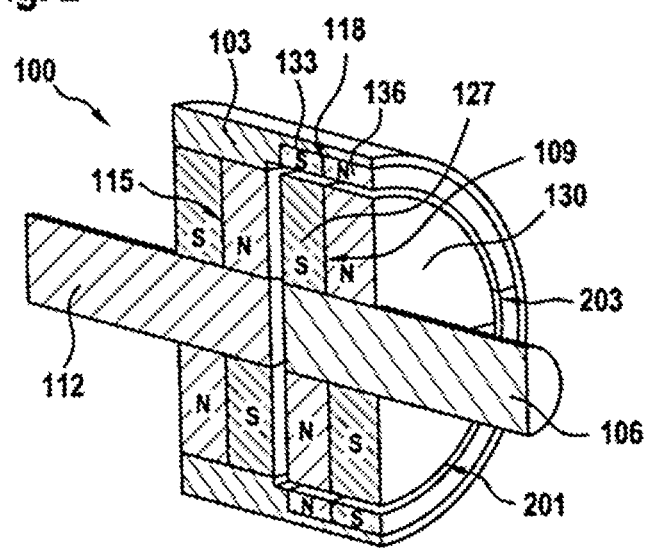
FIG. 2 is a schematic cross-sectional view of a variant of a magnetic coupling element with a magnetic bearing function according to one embodiment.

FIG. 2 is a schematic cross-sectional view of a variant of a magnetic coupling element 100 with a magnetic bearing function according to one embodiment. The magnetic coupling element 100 shown in FIG. 2 can be, for example, a variation of the magnetic coupling element 100 shown in FIG. 1.

The magnetic coupling element 100 comprises the housing element 103, the drive-side coupling magnet 109 arranged on the drive shaft 106, the output-side coupling magnet 115 arranged on the output shaft 112, and the bearing magnet ring 118. The different poles of the coupling magnets 109 and 115 and the bearing magnet ring 118 are indicated with different colors, the north pole being light gray and the south pole being dark gray. The output-side coupling magnet 115 is magnetically coupled to the drive-side coupling magnet 109. The bearing magnet ring 118 is non-rotatably mounted with respect to the drive-side or output-side coupling magnet 109 and 115, the bearing magnet portion 133 and 136 of the bearing magnet ring 118 having the same polarization as the coupling magnet portion 127 and 130 opposite the bearing magnet portion 133 and 136. One bearing magnet portion 201 has an angular offset 203.

The bearing magnet portion 136 has the angular offset 203 with respect to the opposite coupling magnet portion 130 of the drive-side coupling magnet 109. In order to compensate for the rotation of the two shafts 106 and 112 and the coupling magnets 109 and 115 with respect to one another when torque is applied, during the bearing, this can also be provided in the angle-side assignment. An additional bearing magnet ring 118, which is mounted so as to be angularly offset from one of the coupling magnets 109 or 115, makes it possible, in addition to magnetic poles which attract one another in the axial direction and take over the coupling function, to also have repelling poles which oppose one another in the radial direction, and which therefore demonstrate the bearing function.

Figure 3:
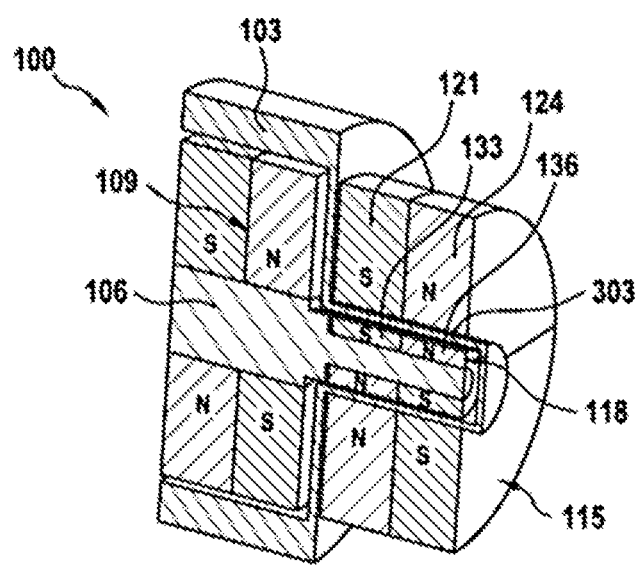
FIG. 3 is a schematic cross-sectional view of a variant of a magnetic coupling element with a magnetic bearing function according to one embodiment.

FIG. 3 is a schematic cross-sectional view of a variant of a magnetic coupling element 100 with a magnetic bearing function according to one embodiment. The magnetic coupling element 100 shown in FIG. 3 can be, for example, a variation of the magnetic coupling element 100 show in FIG. 1 and FIG. 2.

The magnetic coupling element 100 comprises the housing element 103, the drive-side coupling magnet 109 arranged on the drive shaft 106, the output-side coupling magnet 115, and a bearing magnet ring 118. The different poles of the coupling magnets 109 and 115 and the bearing magnet ring 118 are indicated with different colors, the north pole being light gray and the south pole being dark gray. The bearing magnet portion 133 and 136 of the bearing magnet ring 118 has the same polarization or polarity as the coupling magnet portion 121 and 124 opposite the bearing magnet portion 133 and 136.

According to one embodiment, the output-side coupling magnet 115 radially surrounds the bearing magnet ring 118. Between the bearing magnet ring 118 and the output-side coupling magnet 115 there is a tubular portion 303, for example a thin-walled hollow cylinder, of the housing element 103 which separates the bearing magnet ring 118 from the output-side coupling magnet 115. The housing element 103 is made from a non-magnetic metal and/or is formed so as to be non-rotating. The housing 103 results in a separation of media such that, for example in the case of a pump drive, the medium to be pumped cannot reach the interior of the motor.

In general, it can also be stated that the relative strength of the magnets with respect to one other, in particular the relationship between the additional (bearing) magnet ring and the drive-side and output-side coupling magnet, is designed in such a way that, as described above, the repelling forces of the bearing magnetic field also lead to torque and thus to a weakening of the coupling function in the case of axial bearing of the shaft. Therefore, the coupling magnets ought to be designed in such a way that the torque thereof occurring during use is always dominant. The attracting or repelling axial forces as well as flow forces (using the example of a pump) that occur ought to be largely balanced out or absorbed by the axial bearing mentioned above (e.g. ball or slide bearing). Exemplary dimensions of the individual magnetic elements can, in the order of magnitude of the entire coupling in the intended application thereof, involve overall lengths of 3 to 5 mm and diameters of approx. 6 mm. A magnetic strength of the magnets that can be used here can be approximately 1.4 Tesla and can have (temperature-dependent) coercivity field strengths of from −1600 to 0 kA/m.

Figure 4:
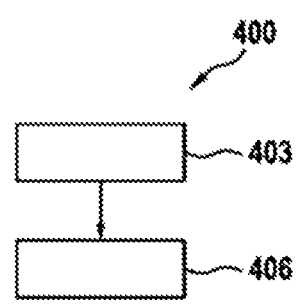
FIG. 4 is a flow chart for one embodiment of a method for producing a magnetic coupling element with a magnetic bearing function according to one embodiment.

FIG. 4 shows a flow chart for one embodiment of a method 400 for producing a magnetic coupling element with a magnetic bearing function according to one embodiment. The method 400 can be designed, using the device for executing the method 400 presented in FIG. 5, to produce a magnetic coupling element with a magnetic bearing function.

In a step 403, the drive-side coupling magnet arranged on a drive shaft, the output-side coupling magnet arranged on an output shaft, and the bearing magnet ring are provided. Finally, in a step 406, the drive-side coupling magnet arranged on a drive shaft, the output-side coupling magnet arranged on an output shaft, and the bearing magnet ring are assembled in such a way that the output-side coupling magnet is magnetically coupled to the drive-side coupling magnet, and the bearing magnet ring is non-rotatably mounted with respect to the drive-side or output-side coupling-magnet, at least one bearing magnet portion of the bearing magnet ring having the same polarity as coupling magnet portion opposite the bearing magnet portion, in order to produce a magnetic coupling element with a magnetic bearing function.

Figure 5:
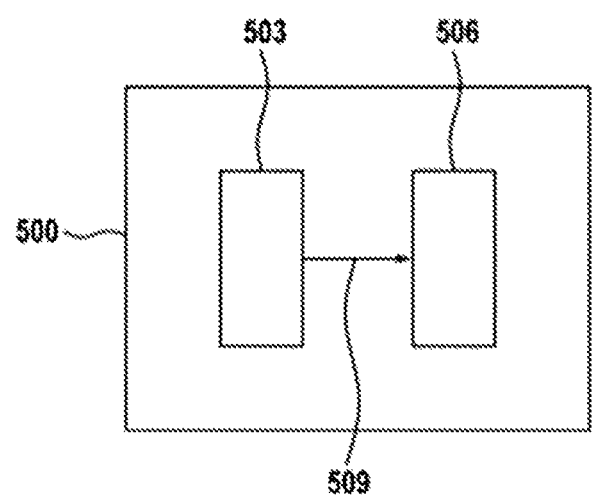
FIG. 5 is a block diagram of a device for executing a method for producing a magnetic coupling element with a magnetic bearing function according to one embodiment.

FIG. 5 shows a block diagram of a device 500 for executing a method for producing a magnetic coupling element with a magnetic bearing function according to one embodiment. The device 500 is designed to execute and/or trigger the steps of the method for producing a magnetic coupling element with a magnetic bearing function in corresponding units.

The device 500 comprises a provision apparatus 503 and an assembly apparatus 506. The provision apparatus is designed to provide a production signal 509 to the assembly apparatus 506 in order to give the assembly apparatus the signal to assemble the individual components of the magnetic coupling element. The provision apparatus 503 is further designed to provide the drive-side coupling magnet arranged on a drive shaft, and also the output-side coupling magnet arranged on an output shaft, and finally the bearing magnet ring. The assembly apparatus 506 is designed to receive the production signal 509 in order to assemble the drive-side coupling magnet arranged on the drive shaft, and also the output-side coupling magnet arranged on the output shaft and finally the bearing magnet ring in such a way that the output-side coupling magnet is magnetically coupled to the drive-side coupling magnet and the bearing magnet ring is non-rotatably mounted with respect to the drive-side or output-side coupling magnet, at least one bearing magnet portion of the bearing magnet ring having the same polarity as a coupling magnet portion opposite the bearing magnet portion, in order to produce a magnetic coupling element with a magnetic bearing function.

If an embodiment comprises an "and/or" conjunction between a first feature and a second feature, this should be understood to mean that the embodiment has both the first feature and the second feature in one form, and has either only the first feature or only the second feature in another form.

What is claimed is:

1. A magnetic coupling element comprising:
   a housing element covering at least a distal portion of a drive shaft;
   an output-side coupling magnet arranged on an output shaft; and
   a bearing magnet arranged on the distal portion of the drive shaft, at least one bearing magnet portion of the bearing magnet having a same polarity as a coupling magnet portion of the output-side coupling magnet located radially of the bearing magnet portion,
   wherein the output-side coupling magnet is located radially outwardly of the housing element that covers the distal portion of the drive shaft, and
   wherein the output-side coupling magnet is located radially outwardly of the bearing magnet.

2. The magnetic coupling element of claim 1, wherein a first magnetic field of the bearing magnet repels a second magnetic field of the output-side coupling magnet in a radial direction.

3. The magnetic coupling element of claim 2, wherein the first magnetic field and the second magnetic field provide a torque to the output-side coupling magnet.

4. The magnetic coupling element of claim 1, wherein the magnetic coupling element is configured to drive an impeller-like rotor.

5. The magnetic coupling element of claim 1, wherein a tubular portion of the housing element covers at least the distal portion of the drive shaft.

6. The magnetic coupling element of claim 5, wherein the tubular portion of the housing element comprises a thin-walled hollow cylinder separating the bearing magnet and the output-side coupling magnet.

7. The magnetic coupling element of claim 6, wherein the housing element is non-rotatable.

8. The magnetic coupling element of claim 1, wherein the bearing magnet is rotatable with respect to the housing element.

9. The magnetic coupling element of claim 8, wherein a rotation of the bearing magnet causes rotation of the output-side coupling magnet.

10. The magnetic coupling element of claim 1, wherein the bearing magnet is a ring.

11. A magnetic coupling element, wherein the magnetic coupling element comprises:
    an output shaft;
    an output-side coupling magnet having a first magnetic field, the output-side coupling magnet arranged on the output shaft;
    a drive shaft; and
    a bearing magnet having a second magnetic field, the bearing magnet arranged on a distal end of the drive shaft, wherein at least one bearing magnet portion of the bearing magnet has a same polarity as a coupling magnet portion of the output-side coupling magnet located radially outwardly of the bearing magnet portion, and wherein the first and second magnetic fields repel one another in a radial direction.

12. The magnetic coupling element of claim 11, wherein the bearing magnet is a ring.

13. The magnetic coupling element of claim 11, wherein the first magnetic field and the second magnetic field provide a torque to the output-side coupling magnet.

14. The magnetic coupling element of claim 11, wherein the drive shaft is configured to rotate the bearing magnet.

15. The magnetic coupling element of claim 14, wherein the output-side coupling magnet is configured to rotate in response to rotation of the bearing magnet.

16. The magnetic coupling element of claim 11, further comprising a housing element covering at least the distal portion of the drive shaft, wherein the housing element separates the bearing magnet and the output-side coupling magnet.

17. A magnetic coupling element comprising:
    a drive shaft;
    a bearing magnet arranged on a distal portion of the drive shaft;
    a housing element covering at least a portion of the bearing magnet and the distal portion of the drive shaft;
    an output shaft;
    an output-side coupling magnet arranged on the output shaft, wherein at least one bearing magnet portion of the bearing magnet has a same polarity as and repels a coupling magnet portion of the output-side coupling magnet, wherein the at least one bearing magnet portion is located radially inwardly of the coupling magnet portion, and
    wherein the output-side coupling magnet at least partially surrounds at least a portion of the housing element such that the output-side coupling magnet is located radially outwardly of the bearing magnet, and wherein the drive shaft is configured to rotate the bearing magnet to thereby cause rotation of the output-side coupling magnet.

18. The magnetic coupling element of claim 17, wherein the bearing magnet is a ring.

19. The magnetic coupling element of claim 17, wherein the magnetic coupling element is configured to drive an impeller-like rotor.

20. The magnetic coupling element of claim 17, wherein a first magnetic field of the bearing magnet repels a second magnetic field of the output-side coupling magnet in a radial direction, and wherein the first magnetic field and the second magnetic field provide a torque to the output-side coupling magnet.

* * * * *